(12) United States Patent
Bauer

(10) Patent No.: US 12,144,993 B2
(45) Date of Patent: *Nov. 19, 2024

(54) HEMODYNAMIC PERFORMANCE ENHANCEMENT THROUGH ASYMPTOMATIC DIAPHRAGM STIMULATION

(71) Applicant: VisCardia, Inc., Beaverton, OR (US)

(72) Inventor: Peter T. Bauer, Portland, OR (US)

(73) Assignee: VisCardia, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/196,148

(22) Filed: May 11, 2023

(65) Prior Publication Data

US 2023/0277855 A1  Sep. 7, 2023

Related U.S. Application Data

(60) Continuation of application No. 17/243,341, filed on Apr. 28, 2021, now Pat. No. 11,684,783, which is a
(Continued)

(51) Int. Cl.
*A61N 1/362* (2006.01)
*A61B 5/00* (2006.01)
(Continued)

(52) U.S. Cl.
CPC ........ *A61N 1/3627* (2013.01); *A61B 5/02438* (2013.01); *A61B 5/113* (2013.01);
(Continued)

(58) Field of Classification Search
CPC ................ A61N 1/3627; A61N 1/3601; A61N 1/36585; A61B 5/02438; A61B 5/113;
(Continued)

(56) References Cited

U.S. PATENT DOCUMENTS 4,411,268 A  10/1983  Cox
5,098,442 A   3/1992  Grandjean
(Continued)

FOREIGN PATENT DOCUMENTS

CA  1256507 A   6/1989
EP  1588735 A1  10/2005
(Continued)

OTHER PUBLICATIONS

Beeler et al. "Improvement of cardiac function with device-based diaphragmatic stimulation in chronic heart failure patients: the randomized, open-label, crossover Epiphrenic II pilot trial." Euro. J. of Heart Failure 16, 342-349 (2014).
(Continued)

*Primary Examiner* — Mallika D Fairchild
(74) *Attorney, Agent, or Firm* — LOZA & LOZA, LLP; David S. Sarisky

(57) ABSTRACT

An implantable system, and methodology, for improving a heart's hemodynamic performance featuring (a) bimodal electrodes placeable on the diaphragm, out of contact with the heart, possessing one mode for sensing cardiac electrical activity, and another for applying cardiac-cycle-synchronized, asymptomatic electrical stimulation to the diaphragm to trigger biphasic, diaphragmatic motion, (b) an accelerometer adjacent the electrodes for sensing both heart sounds, and stimulation-induced diaphragmatic motion, and (c) circuit structure, connected both to the electrodes and the accelerometer, operable, in predetermined timed relationships to the presences of valid V-events noted in one of sensed electrical and sensed mechanical, cardiac activity, to deliver diaphragmatic stimulation. The circuit structure includes accelerometer-linked computer structure for enabling selective review, for later operational modifications, of stimulation-produced diaphragmatic motions, and
(Continued)

in a modified form, may additionally include timing-adjustment substructure capable of making adjustments in the mentioned timed relationships.

16 Claims, 8 Drawing Sheets

Related U.S. Application Data continuation of application No. 16/395,970, filed on Apr. 26, 2019, now Pat. No. 11,020,596, which is a continuation of application No. 15/950,774, filed on Apr. 11, 2018, now Pat. No. 10,315,035, which is a continuation of application No. 15/612,690, filed on Jun. 2, 2017, now Pat. No. 9,968,786, which is a continuation of application No. 15/273,643, filed on Sep. 22, 2016, now Pat. No. 9,694,185, which is a division of application No. 14/107,976, filed on Dec. 16, 2013, now Pat. No. 9,498,625.

(60) Provisional application No. 61/739,704, filed on Dec. 19, 2012.

(51) Int. Cl.
*A61B 5/024* (2006.01)
*A61B 5/113* (2006.01)
*A61B 5/349* (2021.01)
*A61B 5/352* (2021.01)
*A61N 1/36* (2006.01)
*A61N 1/365* (2006.01)

(52) U.S. Cl.
CPC .............. *A61B 5/349* (2021.01); *A61B 5/352* (2021.01); *A61B 5/4836* (2013.01); *A61B 5/686* (2013.01); *A61B 5/6867* (2013.01); *A61B 5/721* (2013.01); *A61B 5/7246* (2013.01); *A61N 1/3601* (2013.01); *A61N 1/36585* (2013.01); *A61B 2562/063* (2013.01)

(58) Field of Classification Search
CPC ....... A61B 5/349; A61B 5/352; A61B 5/4836; A61B 5/686; A61B 5/6867; A61B 5/721; A61B 5/7246; A61B 2562/063
See application file for complete search history.

(56) References Cited

U.S. PATENT DOCUMENTS

| | | |
|---|---|---|
| 5,188,098 A | 2/1993 | Hoffman et al. |
| 5,300,094 A | 4/1994 | Kallok et al. |
| 5,358,519 A | 10/1994 | Grandjean |
| 5,397,280 A | 3/1995 | Skurka |
| 5,632,716 A | 5/1997 | Bui et al. |
| 5,693,000 A | 12/1997 | Crosby et al. |
| 5,758,654 A | 6/1998 | Burton-Krahn et al. |
| 5,814,086 A | 9/1998 | Hirschberg et al. |
| 6,415,183 B1 | 7/2002 | Scheiner et al. |
| 6,979,297 B2 | 12/2005 | Andresen et al. |
| 7,039,538 B2 | 5/2006 | Baker, Jr. |
| 7,072,708 B1 | 7/2006 | Andresen et al. |
| 7,074,195 B2 | 7/2006 | Nelson et al. |
| 7,096,060 B2 | 8/2006 | Arand et al. |
| 7,096,064 B2 | 8/2006 | Deno et al. |
| 7,113,820 B2 | 9/2006 | Schlegel et al. |
| 7,171,269 B1 | 1/2007 | Addison et al. |
| 7,174,203 B2 | 2/2007 | Arand et al. |
| 7,225,021 B1 | 5/2007 | Park et al. |
| 7,248,923 B2 | 7/2007 | Maile et al. |
| 7,277,757 B2 | 10/2007 | Casavant et al. |
| 7,302,290 B2 | 11/2007 | Bauer |
| 7,357,775 B1 | 4/2008 | Koh |
| 7,424,321 B2 | 9/2008 | Wariar et al. |
| 7,435,221 B1 | 10/2008 | Bharmi et al. |
| 7,437,699 B2 | 10/2008 | Morita et al. |
| 7,467,012 B1 | 12/2008 | Park et al. |
| 7,559,903 B2 | 7/2009 | Moussavi et al. |
| 7,668,589 B2 | 2/2010 | Bauer |
| 7,725,181 B1 | 5/2010 | Bornzin et al. |
| 7,819,814 B2 | 10/2010 | Gavriely et al. |
| 7,979,128 B2 | 7/2011 | Tehrani et al. |
| 7,994,655 B2 | 8/2011 | Bauer et al. |
| 8,065,002 B2 | 11/2011 | Arand et al. |
| 8,105,241 B2 | 1/2012 | Nelson et al. |
| 8,137,283 B2 | 3/2012 | Syeda-Mahmood et al. |
| 8,140,164 B2 | 3/2012 | Tehrani et al. |
| 8,185,190 B2 | 5/2012 | Bauer |
| 8,200,336 B2 | 6/2012 | Tehrani et al. |
| 8,233,987 B2 | 7/2012 | Gelfand et al. |
| 8,244,358 B2 | 8/2012 | Tehrani et al. |
| 8,244,359 B2 | 8/2012 | Gelfand et al. |
| 8,265,759 B2 | 9/2012 | Tehrani et al. |
| 8,348,852 B2 | 1/2013 | Bauer et al. |
| 8,409,108 B2 | 4/2013 | Bauer et al. |
| 8,412,323 B2 | 4/2013 | Bauer |
| 8,433,412 B1 | 4/2013 | Westlund et al. |
| 8,548,588 B1 | 10/2013 | Bauer |
| 8,577,448 B2 | 11/2013 | Bauer et al. |
| 8,706,236 B2 | 4/2014 | Ignagni et al. |
| 8,909,341 B2 | 12/2014 | Gelfand et al. |
| 10,335,592 B2 | 7/2019 | Bauer et al. |
| 2002/0103521 A1 | 8/2002 | Swoyer et al. |
| 2002/0188329 A1 | 12/2002 | Struble |
| 2003/0187337 A1 | 10/2003 | Tarassenko et al. |
| 2003/0195571 A1 | 10/2003 | Burnes et al. |
| 2004/0088015 A1 | 5/2004 | Casavant et al. |
| 2004/0127792 A1 | 7/2004 | Siejko et al. |
| 2004/0230105 A1 | 11/2004 | Geva et al. |
| 2005/0027323 A1 | 2/2005 | Mulligan et al. |
| 2005/0043644 A1 | 2/2005 | Stahmann et al. |
| 2005/0065563 A1 | 3/2005 | Scheiner |
| 2005/0080348 A1 | 4/2005 | Stahmann et al. |
| 2005/0085865 A1 | 4/2005 | Tehrani |
| 2005/0085869 A1 | 4/2005 | Tehrani et al. |
| 2005/0090870 A1 | 4/2005 | Hine et al. |
| 2005/0222515 A1 | 10/2005 | Polyshchuk et al. |
| 2006/0079942 A1 | 4/2006 | Deno et al. |
| 2006/0122661 A1 | 6/2006 | Mandell |
| 2006/0122662 A1 | 6/2006 | Tehrani et al. |
| 2006/0155202 A1 | 7/2006 | Arand et al. |
| 2007/0021795 A1 | 1/2007 | Tehrani |
| 2007/0038137 A1 | 2/2007 | Arand et al. |
| 2007/0055151 A1 | 3/2007 | Shertukde et al. |
| 2007/0191725 A1 | 8/2007 | Nelson |
| 2008/0021510 A1 | 1/2008 | Mi et al. |
| 2008/0125820 A1 | 5/2008 | Stahmann et al. |
| 2008/0167695 A1 | 7/2008 | Tehrani et al. |
| 2008/0177191 A1 | 7/2008 | Patangay et al. |
| 2008/0188904 A1 | 8/2008 | Tehrani et al. |
| 2008/0215106 A1 | 9/2008 | Lee et al. |
| 2008/0255465 A1 | 10/2008 | Nelson |
| 2008/0287820 A1 | 11/2008 | Ignagni et al. |
| 2008/0288010 A1 | 11/2008 | Tehrani et al. |
| 2008/0288015 A1 | 11/2008 | Tehrani et al. |
| 2009/0024176 A1 | 1/2009 | Yun et al. |
| 2009/0048640 A1 | 2/2009 | Bauer et al. |
| 2009/0112107 A1 | 4/2009 | Nelson et al. |
| 2009/0112108 A1 | 4/2009 | Nelson et al. |
| 2009/0122108 A1 | 5/2009 | Yoshida et al. |
| 2009/0165559 A1 | 7/2009 | Lec |
| 2009/0192561 A1 | 7/2009 | Bauer |
| 2010/0094148 A1 | 4/2010 | Bauer et al. |
| 2010/0094376 A1 | 4/2010 | Penner |
| 2010/0331903 A1 | 12/2010 | Zhang et al. |
| 2011/0015702 A1 | 1/2011 | Ternes et al. |
| 2011/0230932 A1 | 9/2011 | Tehrani et al. |
| 2011/0288609 A1 | 11/2011 | Tehrani et al. |
| 2012/0103521 A1 | 5/2012 | Cheng |
| 2012/0296388 A1 | 11/2012 | Zhang et al. |
| 2013/0030488 A1 | 1/2013 | Cho et al. |
| 2013/0030498 A1 | 1/2013 | Karamanoglu et al. |

(56) References Cited

U.S. PATENT DOCUMENTS

| | | |
|---|---|---|
| 2013/0289636 A1 | 10/2013 | Karamanoglu et al. |
| 2013/0296973 A1 | 11/2013 | Tehrani et al. |
| 2014/0114371 A1 | 4/2014 | Westlund et al. |
| 2014/0172040 A1 | 6/2014 | Bauer |
| 2017/0143973 A1 | 5/2017 | Tehrani |

FOREIGN PATENT DOCUMENTS

| | | |
|---|---|---|
| JP | 2010537716 A | 12/2010 |
| WO | 2009029172 A1 | 3/2009 |
| WO | 2016033245 A1 | 3/2016 |

OTHER PUBLICATIONS

Matuschak et al. "Hemodynamic effects of syncrhonous high-frequency jet ventilation during acute hypovolemia." J. of Applied Physiology vol. 61:1 44-53 (Jul. 1986).

Pang et al. Monitoring respiratory activity in neonates using diaphragmatic electromyograph. Medical and Biological Engineering and Computing, vol. 33, 385-390 (1995).

Pinsky et al. "Hemodynamic effects of cardiac cycle-specific increases in intrathoracic pressure." J. of Applied Physiology vol. 60:2, 604-612 (Feb. 1986).

Pinsky et al. "Augmentation of cardiac function by elevantion of intrathoracic pressure." J. of Applied Physiology, vol. 54:4, 950-955 (Apr. 1983).

Pinsky et al. "Determinants of cardiac augmentation by elevations in intrathoracic pressure." J. of Applied Physiology vol. 58:4, 1189-1198 (Apr. 1985).

Roos, Markus, et al; Improved cardiac performance through pacing-induced diaphragmatic stimulation: a novel electrophysiological approach in heart failure management? European Society of Cardiology. Clinical Research. Pacing and Cardiac Resynchronization Therapy. Europace (2009) 11, 191-199. Dec. 8, 2008. Luzern, Switzerland.

Zuber, Michel, et al; Detection and Hemodynamic Significance of Cardiac Pacemaker-Induced Phrenic Nerve Stimulation. Department of Cardiology, Kantonsspital, Luzern, Switzerland. 2010 Wiley Periodicals, Inc. Aug. 13, 2009. Luzern, Switzerland.

JP Application No. 2015-549544. Office Action (Sep. 21, 2017).

EP Application No. 13865191.4. Office Action (Sep. 29, 2017).

PCT/US2013/075489. International Search Report & Written Opinion (Mar. 11, 2014).

PCT/US2013/075489. International Preliminary Report on Patentability (Jun. 23, 2015).

PCT/US2017/029905. International Search Report & Written Opinion (Aug. 8, 2017).

PCT/US2017/029905. International Preliminary Report on Patentability (Aug. 22, 2018).

PCT/US2017/029924. International Search Report & Written Opinion (Oct. 2, 2017).

PCT/US2017/029924. Written Opinion of the International Preliminary Examining Authority (Apr. 6, 2018).

PCT/US2017/029924. International Preliminary Report on Patentability (Aug. 10, 2018).

PCT/US2017/029939. International Search Report & Written Opinion (Aug. 10, 2017).

PCT/US2017/029939. Written Opinion of the International Preliminary Examining Authority (Apr. 6, 2018).

PCT/US2017/029939. International Preliminary Report on Patentability (Oct. 12, 2018).

PCT/US2017/051021. International Search Report & Written Opinion (Dec. 12, 2017).

PCT/US2017/051021. Written Opinion of the International Preliminary Examining Authority (Aug. 24, 2018).

PCT/US2017/051021. International Preliminary Report on Patentability (Jan. 3, 2019).

PCT/US2020/052246. Annex Partial International Search Report (Dec. 16, 2020).

HEMODYNAMIC PERFORMANCE ENHANCEMENT THROUGH ASYMPTOMATIC DIAPHRAGM STIMULATION

CROSS-REFERENCE TO RELATED APPLICATIONS

This application is a continuation of U.S. patent application Ser. No. 17/243,341, filed Apr. 28, 2021, for "Hemodynamic Performance Enhancement Through Asymptomatic Diaphragm Stimulation," now U.S. Pat. No. 11,684,783 issued Jun. 27, 2023, which is a continuation of U.S. patent application Ser. No. 16/395,970, filed Apr. 26, 2019, for "Hemodynamic Performance Enhancement Through Asymptomatic Diaphragm Stimulation," now U.S. Pat. No. 11,020,596 issued Jun. 1, 2021, which is continuation of U.S. patent application Ser. No. 15/950,774, filed Apr. 11, 2018, for "Hemodynamic Performance Enhancement Through Asymptomatic Diaphragm Stimulation," now U.S. Pat. No. 10,315,035 issued Jun. 11, 2019, which is a continuation of U.S. patent application Ser. No. 15/612,690, filed Jun. 2, 2017, for "Hemodynamic Performance Enhancement Through Asymptomatic Diaphragm Stimulation," now U.S. Pat. No. 9,968,786 issued May 15, 2018, which is a continuation of U.S. patent application Ser. No. 15/273,643, filed Sep. 22, 2016, for "Hemodynamic Performance Enhancement Through Asymptomatic Diaphragm Stimulation," now U.S. Pat. No. 9,694,185 issued Jul. 4, 2017, which is a divisional of U.S. patent application Ser. No. 14/107,976, filed Dec. 16, 2013, for "Hemodynamic Performance Enhancement Through Asymptomatic Diaphragm Stimulation," now U.S. Pat. No. 9,498,625 issued Nov. 22, 2016, which claims the benefit of and priority to U.S. Provisional Patent Application Ser. No. 61/739,704, filed Dec. 19, 2012, for "Hemodynamic Performance Enhancement Through Asymptomatic Diaphragm Stimulation to the Diaphragm/Heart Interface," the entire disclosures of which are incorporated herein by reference.

BACKGROUND AND SUMMARY OF THE INVENTION

The present invention pertains to an implantable medical system, and to an associated methodology, employing, and managed by electrical circuit structure, which features logic-including, internal-control circuitry referred to herein as computer structure, or more simply as a computer, for enhancing hemodynamic performance in subjects with cardiac disease through applying carefully timed, regular, per-cardiac-cycle, synchronized, asymptomatic, electrical pulsed stimulation to the diaphragm intended to induce short-term occurrences of biphasic diaphragmatic motion. In particular, it relates to such a system and methodology which, in relation to each such stimulation, and through operation of the included control circuitry (which forms part of what is referred to as electrical circuit structure), monitors and records information regarding resulting, induced diaphragmatic-motion for later review, and to accommodate potential, telemetry-adjusted, systemic-performance adaptation to improve diaphragmatic stimulation characteristics so as to maximize the sought hemodynamic-performance enhancement. The system preferably additionally permits, in a modified form, selective, remote-telemetry-implemented communication from outside the anatomy to allow for other kinds of system-behavioral adjustments, such as ones that relate to timing matters.

The term "hemodynamic performance" is used synonymously herein with the terms "cardiovascular performance" and "cardiac function". The biphasic diaphragmatic motion produced by electrical stimulation, in accordance with practice of the invention, is what is called herein caudal-followed-by-cranial motion of the diaphragm. The included "computer-structure" logic componentry, which may be hard-wired to perform its intended functions, or more preferably fully or partially programmable, as by telemetry, may also feature an appropriate microprocessor. It may also include, or be appropriately internally associated with, a suitable "state machine" for implementing various important timing controls, as will be explained below.

Pulsed stimulation of the type just above mentioned, properly characterized and applied, triggers, in each case, a very short (only a few tens of milliseconds) pulse-like, biphasic (singular-caudal-followed-by-singular-cranial) motion of the diaphragm, and, relatedly also, a substantially following pumping-relevant motion of the left ventricle in the heart which rests on the diaphragm. This stimulation creates this motion-generating activity in a manner which, when properly and synchronously timed in relation to the onset of left-ventricular contraction, improves hemodynamic performance through enhancing the important cardiac pumping functions of both (a) late diastolic filling, and (b) early systolic contraction.

Asymptomatic stimulation implemented in the practice of the present invention is also referred to herein as PIDS stimulation—the acronym PIDS standing for the phrase "pacing induced diaphragmatic stimulation". The mentioned monitoring and recording for later stimulation-characteristic review, and possible revision purposes, are linked with systemically control-circuitry-performed comparing of actual induced diaphragmatic-motion waveforms with a provided and internally stored reference waveform.

Of key importance in all featural expressions of the present invention, systemic and methodologic, are (1) that sensing of what is referred to herein as a valid electrical or mechanical V-event, and (2) that related, sensing-based, ultimate applying of electrical stimulation to the diaphragm, take place, with the system installed for use with a subject, from an implanted systemic disposition directly adjacent, and preferably in contact with, a selected surface region in the subject's diaphragm. Preferably, but not necessarily, this selected surface region, which may be either an inferior (preferred), or a superior, surface region in the diaphragm, and which may be chosen to be at many different, diaphragmatic surface locations, is disposed left-lateral relative to the subject's anatomy—and under all circumstances, out of contact with the heart.

A V-event, in either category (electrical or mechanical), is defined herein as being either the onset of left-ventricular contraction, or a cardiac electrical or mechanical event having a predictably known relationship to such an onset. A valid electrical V-event is treated as being either the electrical R or Q wave, and a valid mechanical V-event is treated as being the S1 heart sound. Cardiac-cycle-by-cardiac-cycle, synchronized, diaphragmatic stimulation is timed, selectively in different ways—anticipatory (early), or following (late)—in relation to per-cardiac-cycle, detected, valid V-events.

Of special importance in certain featural expressions of the present invention, systemic and methodologic, is the effective incorporation in the proposed system and associated methodology of a focus, through the use of a system-included accelerometer, preferably multi-axial in character, and even more preferably three-dimensional in nature, on the monitoring and recording of the mechanical waveform of per-cardiac-cycle, mechanical diaphragmatic biphasic motion which is actually produced by applied, electrical diaphragmatic stimulation in comparison with a pre-set, diaphragmatic-motion reference waveform. Information regarding non-conformance of these two waveforms—computer acquired and recorded according to the invention—is important for periodic system-performance review, and in this context, is very useful to support the making, when desired, of appropriate, per-cardiac-cycle, electrical stimulation-character modifications to enhance such performance.

It should be noted that while different embodiments of the invention may use different-axial-sensitivity accelerometers, preferred in most applications is the inclusion and use of a three-dimensional, i.e., three-axis, accelerometer. Accordingly, the preferred systemic and methodologic invention descriptions presented herein below are described in the context of employment of a three-dimensional accelerometer.

Two, principal, implantable systemic forms, or embodiments, of the invention are proposed, one of which features, as an entirety—i.e., as a singularity—a self-contained, self-powered, singular capsule construction, and the other of which features a distribution, also self-powered, of components organized into two arrangements of components separated by an interconnecting, cross-communication lead structure.

Other forms of the invention, not pictured or discussed herein, and differing specifically from the two, just-mentioned currently principal, preferred forms, are recognized to be very suitably possible to address different implantation applications, wherein the various system components, described below for the two invention forms particularly set forth herein, become organized in different implantable ways.

Regarding systemic performance functionality in the context of the present invention disclosure, the same, basic invention methodology, in terms of the important, end-result achieving of hemodynamic/cardiovascular performance enhancement through triggered pulses of biphasic motion introduced into the diaphragm (as above outlined), is implemented in both of the specifically herein described systemic invention forms.

Stimulation-induced diaphragmatic movements, as just generally described above, are, in relation to normal respiration-motion frequency (typically about 0.2-0.3-Hz), and as mentioned, short-term, relatively high-frequency (typically about 12-15-Hz), pulse-like motions. These quick motions are superimposed on the regular, and much lower frequency, diaphragmatic respiration movements. The initial, short-term caudal movement effected by diaphragmatic stimulation pulls on the left ventricle, and if well timed, such stimulation-resulting "pulling" increases the atrial contribution to left-ventricular filling during late diastole (i.e., a so-called "atrial kick") with a resulting subsequent increase in stroke volume via the recognized, Frank-Starling mechanism. The secondary, stimulation-induced movement of the diaphragm which is cranial, and which is also much faster than regular diaphragmatic respiratory motion, causes the left ventricle to be "kicked" upwardly, and If this secondary movement occurs in the early part of systole, and prior to the closure of the mitral valve, it enhances cardiac function further by increasing the momentum of ventricular contraction.

Accordingly, in relation to achieving desired hemodynamic-enhancement, it is important to optimize the timing between the onset of ventricular contraction and diaphragmatic stimulation so that the actual timing and impact of the mentioned caudal and cranial components of motion as they affect cardiac function are maximized. Such maximizing is subject-specific, in relation, of course, to a given subject's particular cardiac structure (electrically and mechanically), and accordingly, medically-determined, properly associated, subject-specific timing requirements are initially "set into the system of the invention", as will be explained. When all operational parameters are properly "put in place", the present invention successfully accomplishes appreciable hemodynamic-performance optimization.

As mentioned above, two, fully implantable, and fully self-powered, principal embodiments of the system of the present invention are specifically illustrated and described herein, one of which, as stated above, is a single-unit, self-contained, capsule-form arrangement, and the other of which has a distributed-component, communication-lead-line-interconnecting form.

According to one manner of describing generally the structural nature of the present invention, what is proposed is a system including (a) bi-modal (cardiac-electrical-activity sensing in one mode, and related diaphragmatic electrical stimulating in the other mode) electrode structure operatively connectable to a selected surface region in a subject's diaphragm, and (b) monitoring and controlling circuit structure which is connected to the electrode structure, and operable (1) to receive and process electrode-structure-sensed electrical cardiac activity when the electrode structure, under the influence of the circuit structure, is functioning in its sensing mode, and (2), based on such receiving and processing, to communicate to the diaphragm via the electrode structure, when the latter is functioning, also under the influence of the circuit structure, in its stimulating mode, appropriate diaphragmatic stimulation.

In a more particular sense respecting this just-above-presented systemic expression of the invention, (a) the selected, diaphragmatic surface region is disposed (1) preferably, but not necessarily, at a location which is lateral, and even more specifically left-lateral, within a subject's anatomy, and (2) in all instances out of contact with, the subject's heart, and (b) the mentioned circuit structure includes computer structure which specifically operates, relative to the circuit structure's delivery of electrical stimulation through the electrode structure, to control appropriately predetermined timed relationships relative to noted presences, in received and monitored cardiac-cycle electrical-activity information, of valid electrical V-events. Additionally, contemplated in the practice of the invention are two, different categories of such predetermined timed, or timing, relationships, one of which involves anticipation of a next-expected, valid, cardiac-cycle, electrical V-event, and the other of which involves a following of the last-sensed, valid, cardiac-cycle, electrical V-event. These same, two categories of timing relationships are equally applicable to another form of the system of the invention, discussed below, which further includes an accelerometer (single or plural-axis), also referred to herein as a mechanical sensing structure, that is designed to detect heart sounds, and in particular S1 heart sounds, as valid mechanical V-events.

An augmented form (the "another form" of the invention mentioned immediately above) of this just-presented description of the invention is one in which the proposed system further includes specifically a three-dimensional accelerometer (called also a mechanical sensing structure), (a) disposed adjacent, and operatively associated with, the electrode structure for contact-associated disposition in a motion-sensing relationship with, and with respect to, the subject's diaphragm, (b) operatively connected to the mentioned circuit structure, and (c) constructed to be responsive to any motion produced in the subject's diaphragm as a consequence of electrical diaphragmatic stimulation, and in relation to such responsiveness, to generate and communicate to the circuit structure a diaphragmatic-motion confirmation signal possessing a waveform which is directly indicative of such motion.

In a further way of thinking about the accelerometer-including system form of the invention, the circuit structure's included computer structure features a waveform monitoring and recording substructure for comparing the waveform of a communicated confirmation signal with a reference waveform, and recording the conformation-signal waveform for subsequent review.

Another way of thinking about the invention, in relation to the inclusion therein of an accelerometer, is that, in accordance with a modified form of the invention, (a) an included accelerometer functions, additionally, for sensing, in a subject's cardiac cycles, cardiac-cycle, S1 heart-sound, mechanical activity—a valid mechanical V-event—which is discernible at the selected, diaphragmatic surface region, and that (b), the included circuit structure receives this mechanical valid V-event information from the accelerometer, and is operable, in predetermined timed relationships to noted presences, in such received mechanical S1-heart-sound, of valid V-event information, to deliver asymptomatic electrical stimulation through the electrode structure to the subject's diaphragm for the purpose of triggering the intended biphasic, caudal-followed-by-cranial, motion of the diaphragm.

A further modified form of the basic system of the invention, contemplated for implementation in certain applications, and representationally pictured, described and included herein in each of the two principal embodiments disclosed, is one wherein the computer structure which forms part of the included circuit structure possesses timing-adjustment substructure capable of making an adjustment periodically in the predetermined timed relationship which determines when, in relation to a sensed, valid V-event, electrical diaphragmatic stimulation occurs. This modification is versatile in its utility, offering the possibility of adjusting, either remotely, or internally automatically if desired, such stimulation timing in a manner aimed at further enhancing a subject's hemodynamic performance if, and as, the subject's heart-behavior conditions change over time.

These and other systemic aspects of the invention, preferred and modified, are discussed below herein.

From a methodologic point of view the invention offers a method for improving the hemodynamic performance of a subject's heart including, from adjacent a selected surface region in the subject's diaphragm which is out of contact with, the heart, (1) sensing and noting the presences in the subject's cardiac cycles of a selected one of (a) per-cycle valid electrical, and (b) per-cycle valid mechanical, V-events, (2) based upon such sensing, and upon noting each of such selected, V-event presences, applying, in a predetermined timed relationship to such a noting, associated, asymptomatic electrical stimulation directly to the diaphragm, preferably at the selected diaphragmatic surface region, for the purpose of triggering biphasic, caudal-followed-by-cranial motion of the diaphragm, (3) following the applying step, monitoring the waveform of resulting diaphragmatic motion, (4) after performing the monitoring step, comparing the monitored diaphragmatic-motion waveform with a reference, diaphragmatic-motion waveform, and (5) on completion of the comparing step, recording the monitored, diaphragmatic-motion waveform for later review.

The invention methodology further includes (1) choosing the selected diaphragmatic surface region to be on one of (a) the inferior, and (b) the superior, side of the diaphragm, and (2) choosing the selected, per-cycle valid V-event whereby, if it is to be electrical, it is one of (a) the R wave, and (b) the Q wave, and if mechanical, it is the S1 heart sound.

These and various other features and advantages that are offered by the system and methodology of the present invention will become more fully apparent as the detailed description of the invention which follows below is read in conjunction with the accompanying drawings.

BRIEF DESCRIPTION OF THE DRAWINGS

FIG. 7A pictures a condition of asymptomatic-stimulation-produced caudal diaphragmatic motion, and FIG. 7B a condition of related, immediate-time-following, cranial diaphragmatic motion.

Figure 6A:
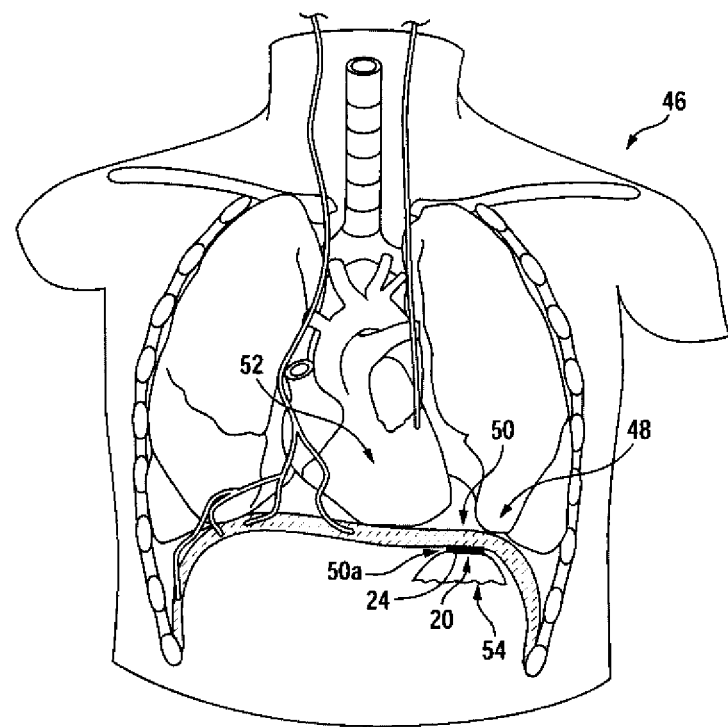
FIG. 6A is a frontal view of an internal portion of a subject's anatomy illustrating preferred, implanted positioning therein proposed for the system embodiment shown in FIGS. 1-4, inclusive.
Figure 6B:
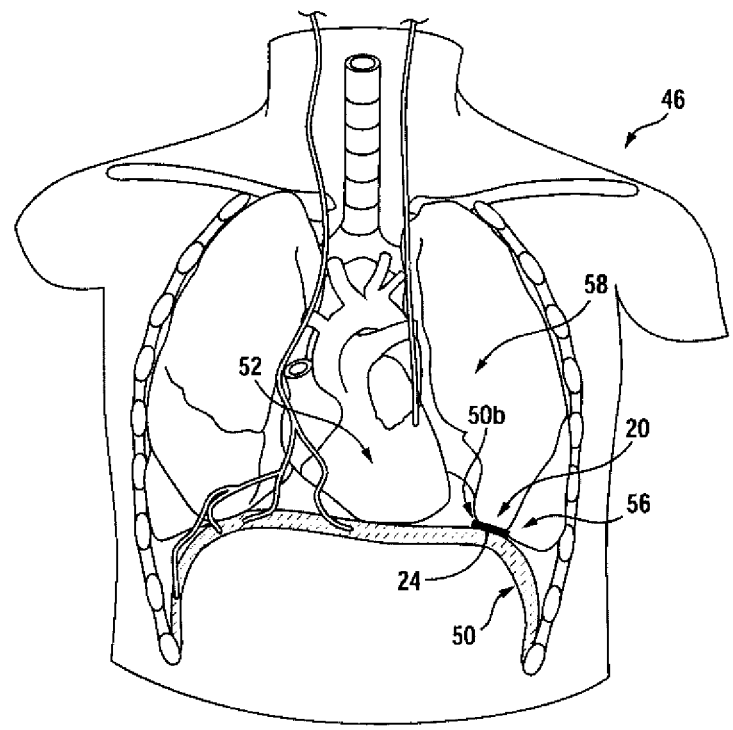
FIG. 6B is similar to, and is drawn on about the same scale as that employed in, FIG. 6A, except that it shows an alternative placement in the anatomy for the system of FIGS. 1-4, inclusive.
Figure 7A:
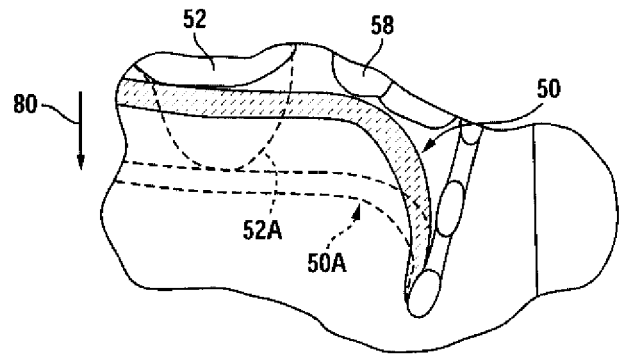
FIGS. 7A, 7B present enlarged-scale, fragmentary portions of the anatomical structure shown in FIGS. 6A, 6B, with the system of FIGS. 1-4, inclusive, removed for clarity purposes, illustrating, specifically, biphasic mechanical movement, or motion, of the heart resulting from electrical stimulation, and resulting mechanical motion, of the diaphragm and heart in accordance with practice of the methodology of the present invention.
Figure 7B:
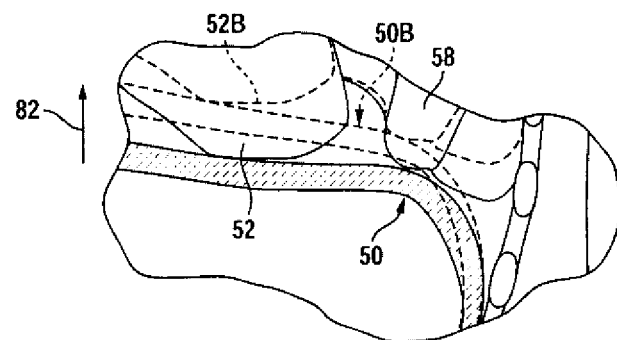
Figure 9A:
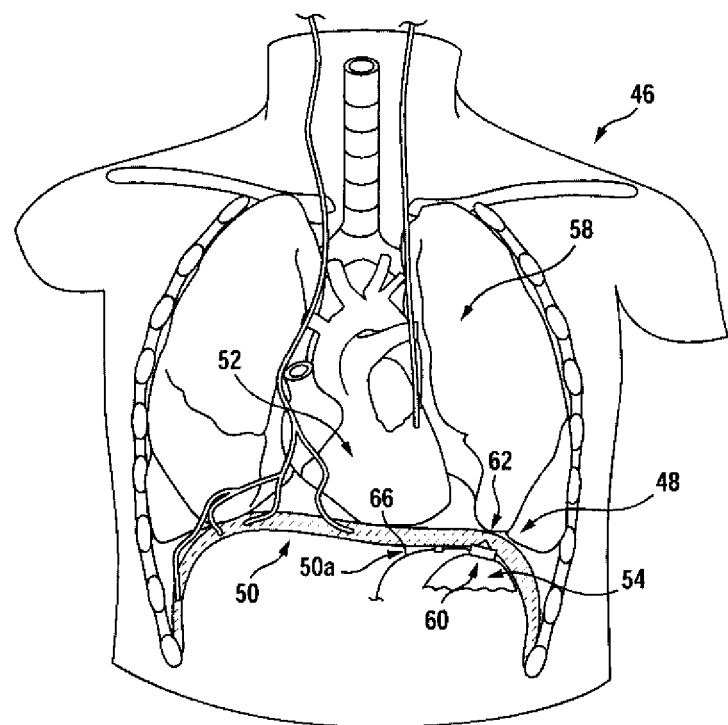
Figure 9B:
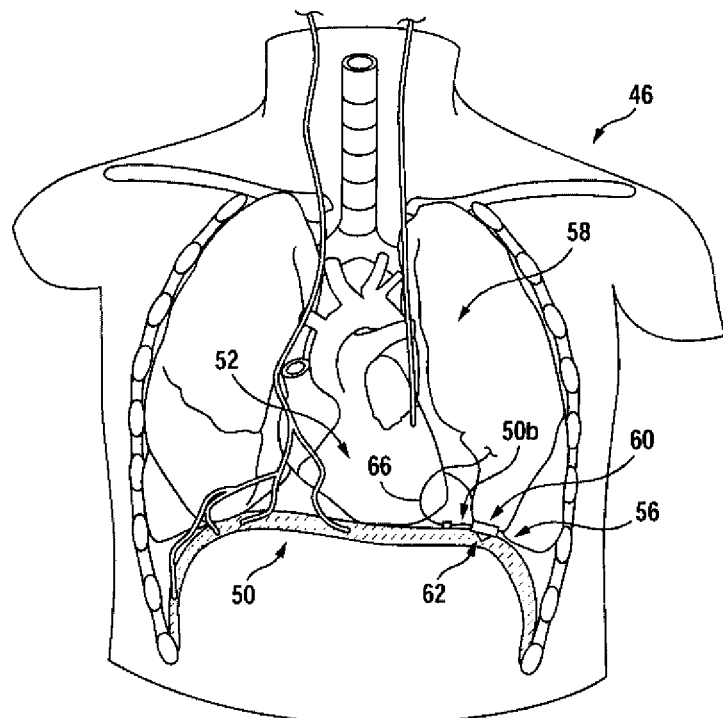

The statements just made, which draw relationships between conditions pictured in FIGS. 7A, 7B, with respect to FIGS. 6A, 6B, respectively, are equally applicable to relationships that exist between FIGS. 7A, 7B, and still-to-be-described FIGS. 9A, 9B.

Figure 8:
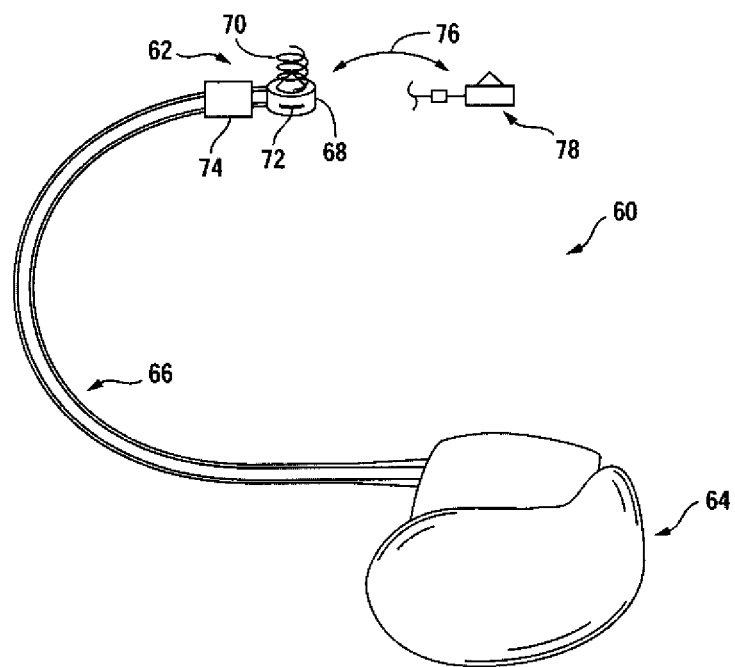

FIG. 8 illustrates an alternative, fully implantable systemic embodiment of the present invention—one which has a distributed structural characteristic resulting from the condition that certain components in this embodiment are arranged in two assemblies that are separated from one another by an interconnecting communication lead structure.

FIGS. 9A, 9B are similar to FIGS. 6A, 6B, respectively, differing in that they illustrate two, alternative, proposed internal anatomical placements for certain ones of the components included in the embodiment of the invention pictured in FIG. 8.

In FIGS. 6A, 6B, 9A and 9B, the exposed anatomical contents are greatly simplified in order to avoid unnecessary complexity without compromising disclosure necessity, and in this context, lower portions of the left-side phrenic nerve structure have been removed to afford better viewing clearance to see the positioning illustrated therein for implanted system structure.

The various structural and anatomical elements shown in FIGS. 1-7B, inclusive, and in FIGS. 9A and 9B, and the several moved anatomical positions, and changed anatomical configurations, pictured in FIGS. 7A and 7B, are not necessarily drawn to scale.

Figure 10:
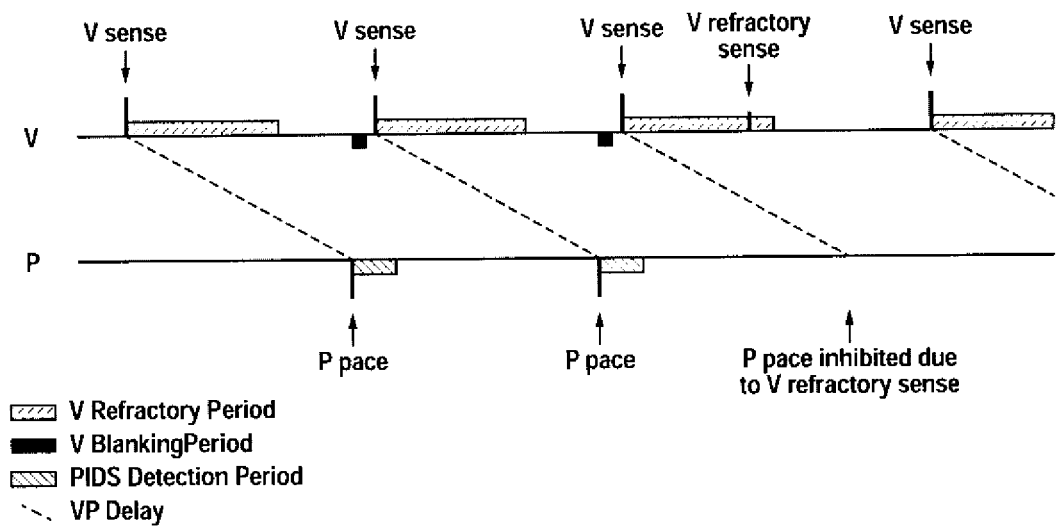
Figure 11:
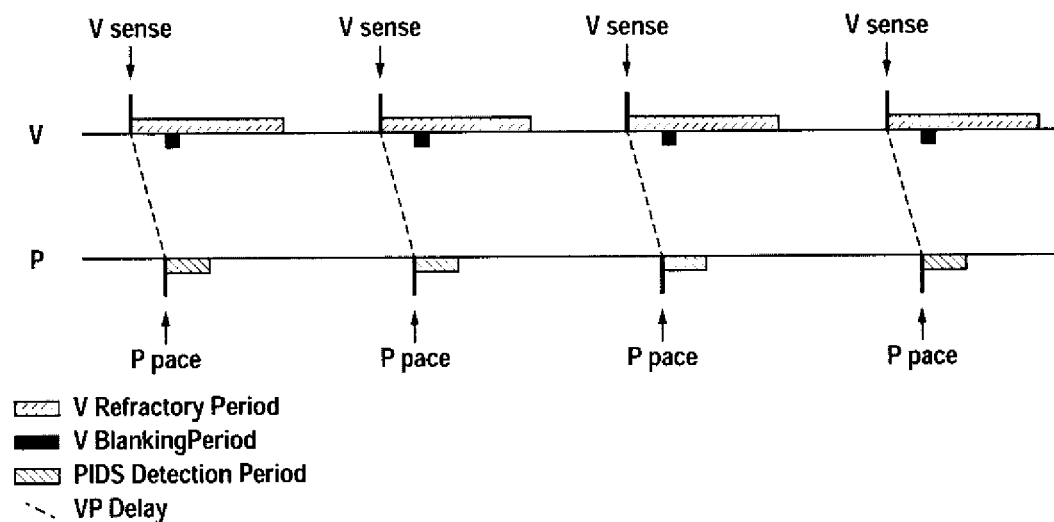

FIGS. 10 and 11 present two, different, laddergram illustrations picturing, respectively, what are referred to herein as early diaphragmatic, and late diaphragmatic, electrical stimulation.

Figure 12:
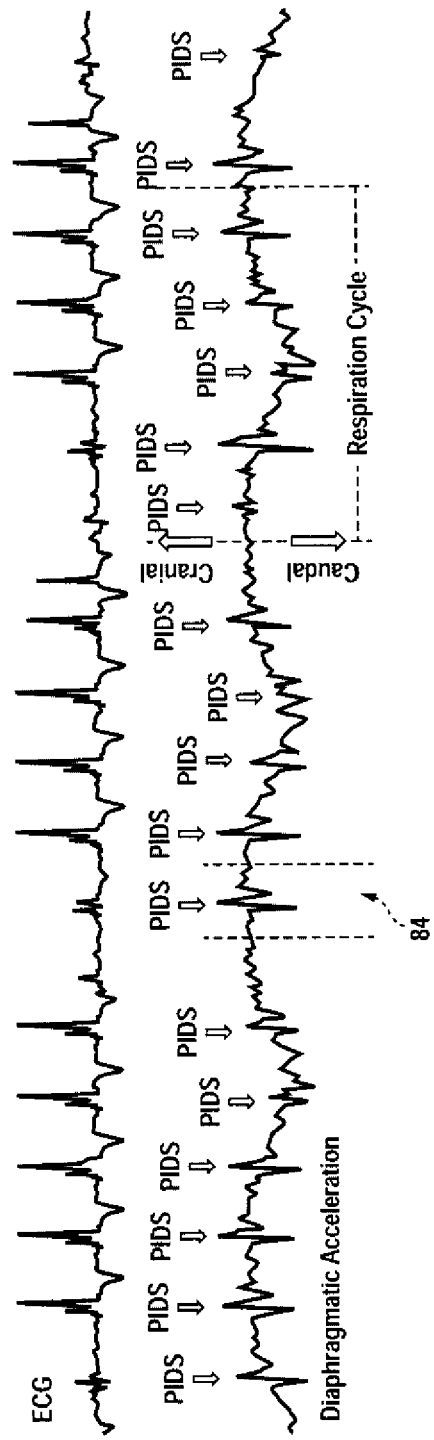

FIG. 12 is a two-trace, common-time-base, graphical presentation relating to electrical V-event sensing, associated cardiac-cycle-synchronized, diaphragmatic stimulation, and resulting diaphragmatic and left-ventricle biphasic mechanical motions.

Figure 13:
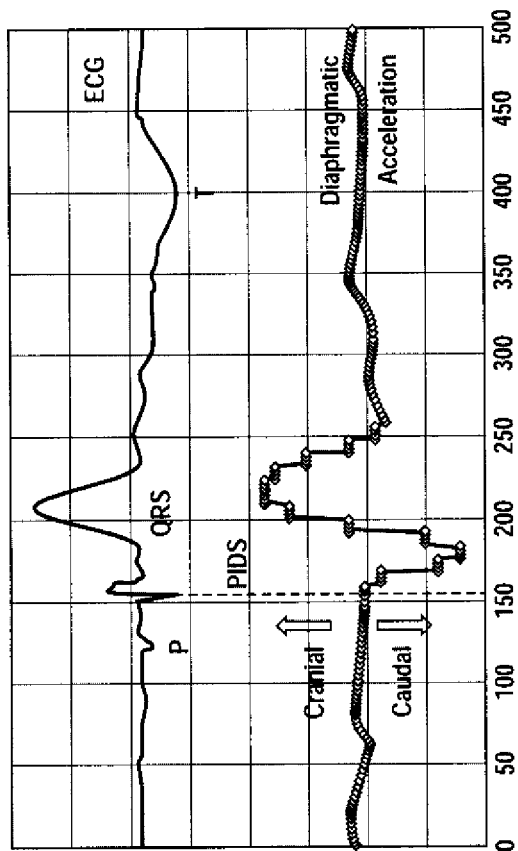

FIG. 13 furnishes an enlarged view of a single cardio cycle event pictured between a pair of spaced, vertical, short dashed lines in FIG. 12.

Figure 14:
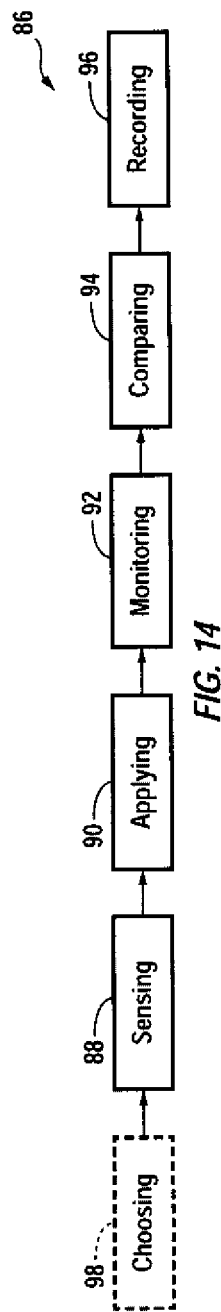

FIG. 14 is a high-level, block/schematic diagram illustrating both the basic, and one modified, form of the architecture of the methodology of the present invention.

DETAILED DESCRIPTION

Turning now to the drawings, and referring first of all to FIGS. 1-5, inclusive, indicated generally at 20 is one preferred form of a self-contained, self-powered, fully implantable medical system constructed in accordance with the present invention for improving the hemodynamic performance of a subject's heart. System 20 accomplishes such improvement, as will be explained, through applying specially timed, cardiac-cycle-synchronized, asymptomatic, electrical stimulation directly to the subject's diaphragm to produce very short duration, relatively high-frequency (as mentioned above), bi-phasic motion of the diaphragm, which motion becomes communicated/applied directly to the underside of the left ventricle in the heart to create, essentially, a diaphragmatic-motion-following, bi-phasic "pumping" motion in and for the underside of, and thus within, the left-ventricle.

System 20, as seen in FIGS. 1-4, inclusive, has what is referred to herein as a singular capsule form 22. This form features a small, easily implantable, elongate, thin, non-electrically-conductive, and appropriately biocompatible capsule body, or capsule, 24 having the shape shown, with a length herein of about 1.25-inches, a width of about 0.5-inches, and a thickness of about 0.125-inches. Body 24, has a hollow interior 24a (see FIGS. 3 and 4), and possesses an elongate, outside, diaphragm-contacting face 24b (see FIGS. 1 and 2), also referred to herein as an electrode face, near the opposite ends of which are positioned two, spaced (by about 1-inches), and outwardly exposed, bimodal electrodes 26, 28, referred to collectively herein as bimodal electrode structure. Electrodes 26, 28 present exposed, circular faces 26a, 28a, each having a diameter herein of about 0.15-inches. Generally speaking, these electrodes function, in an implanted-condition operation of system 20, both to sense heart-related electrical activity—done in a so-called first, or one, mode of operation, and to apply controlled, asymptomatic, electrical stimulation to the diaphragm—done in a so-called second, or other, independent mode of operation.

The specific capsule shape illustrated in FIGS. 1-4, inclusive, and the several specific dimensions just mentioned, are not critical, and may be varied selectively according to user wishes to suit different, particular implantation applications. What is important, of course, is that the shape and dimensions of capsule 24 be suitable and comfortable, and designed for minimally invasive placement for operational residence within a subject's anatomy. As will be explained below, while preferred placement involves, effectively, stabilized attachment to a surface region which is near the upper portion of a subject's diaphragm (inferior or superior), there may be other diaphragmatic locations that are suitable for placement. The same statements just made about shape and sizing, addressed initially specifically herein with respect to the capsule form of the invention now being discussed, are also applicable to a still-to-be-described, second preferred embodiment pictured in FIG. 8. Respecting each of the two, principal forms of the invented system disclosed herein, while users/installers of it may readily choose various, different, appropriate, and preferably minimally-invasive, surgical procedures to carry out implantation within a subject's anatomy, laparoscopy is considered to be a good choice for system placement on the inferior side of the diaphragm, and thoracotomy, a good choice for such placement on the superior side of the diaphragm.

A suitable, conventional, non-electrically-conductive, biocompatible mesh 30 (see FIGS. 1 and 2), is affixed to capsule face 24b to facilitate, following system implantation, natural-process anatomical bonding, for positional stabilization, to a selected surface region (inferior or superior) in/on a subject's diaphragm. Inclusion of such a mesh is optional, but useful. As will be further discussed, inferior surface-region placement on the diaphragm is preferred, and also preferably, though not necessarily, at a diaphragmatic location which is left-lateral in a subject's anatomy. Additionally, under all circumstances involving superior surface-region placement, such placement should be one where capsule 24 is out of direct contact with the heart.

Included in system 20, housed within the hollow interior 24a in capsule body 24, are various electrical and mechanico-electrical, system-operational components, including an electrical circuit structure 32 which, through the included presence in it of logic-including, internal-control circuitry (still to be pointed out in the drawings), manages all system electrical-performance activity, a battery 34 which furnishes all needed operating power for the system, and a multi-axial (three-dimensional herein) accelerometer, or mechanical sensing structure, 36 which, with the system in an appropriate anatomically implanted condition, senses a variety of mechanical and sound activities, such as diaphragmatic-motion activities, and heart sounds. Regarding the accelerometer's sensing of diaphragmatic-motion activity, a sensing capability enhanced by its proposed, and intended, implanted placement in what is referred to herein as a motion-sensing relationship directly on the diaphragm, it produces an important electrical, diaphragmatic-motion confirmation signal for delivery to electrical circuit structure 32, which signal is directly indicative of the waveform of such motion. This signal is significantly useful for assuring that actually applied electrical diaphragmatic stimulation is as best-suited as possible for triggering the desired biphasic diaphragmatic movement intended to maximize hemodynamic performance enhancement. This assuring comes about because, according to the methodology of the present invention, the waveform represented by the accelerometer's supplied confirmation signal is regularly compared with a reference waveform "known" to the system of the invention.

Heart sounds sensed by the included accelerometer are useful for many purposes, and especially the S1 heart sound which is used, in an already (above) mentioned, modified form of the invention to act, and be recognized as, a valid mechanical V-event in relation to which appropriate timing for the application of a diaphragmatic stimulation is measured.

Other interesting information which may be obtained, if desired, from the response of the system-included accelerometer, not directly related to the practice and methodology of the present invention, but nevertheless available, for example, to a physician monitoring various subject conditions that may, in different ways, have a relationship to hemodynamic performance, include subject activity levels, subject body posture, respiratory information, such as respiration rate, sleep-disordered breathing events, heart murmurs, and perhaps others.

Figure 1:
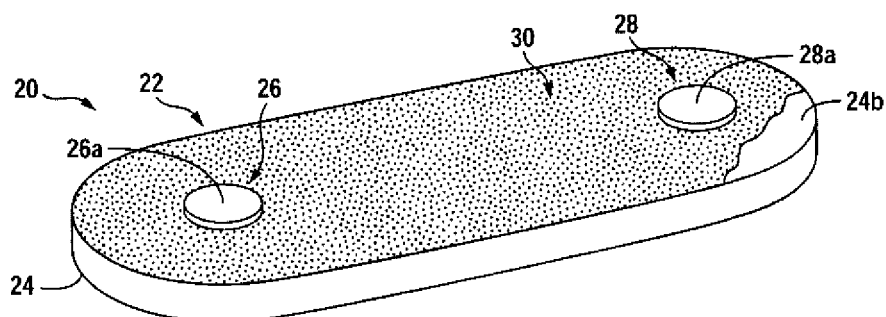
FIG. 1 is an isometric, electrode-side, facial view of a fully implantable fully self-contained, self-powered, singular capsule-form embodiment of the system of the present invention.
Figure 2:
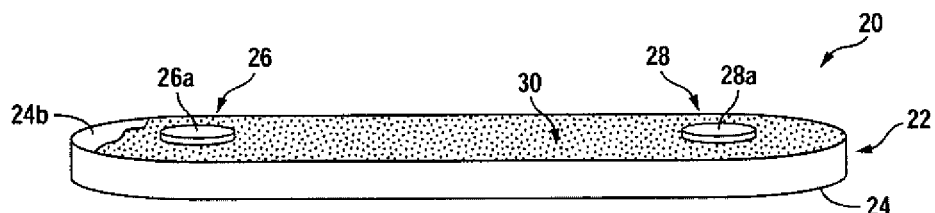
FIG. 2 is a same-scale, lateral isometric view of the embodiment shown in FIG. 1, slightly rotated about two axes relative to what is seen in FIG. 1.
Figure 3:
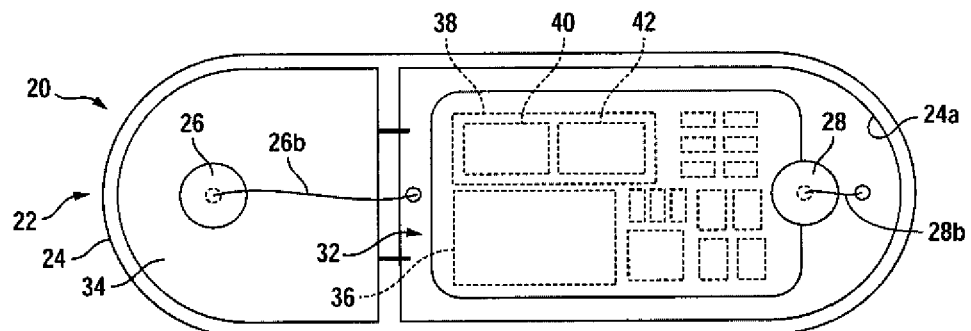
FIG. 3 is a plan view of the invention embodiment shown in FIGS. 1 and 2, drawn on about the same scale used in these two figures, and pictured with the body of the capsule in this embodiment opened to show internally contained electrical circuitry, an accelerometer, and an included battery.
Figure 4:
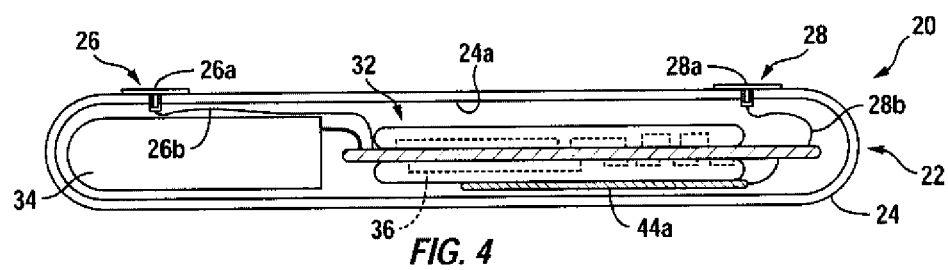
FIG. 4, which uses the same drawing scale as that seen in FIG. 3, is a lateral cross section taken generally from the lower side of FIG. 3.
Figure 5:
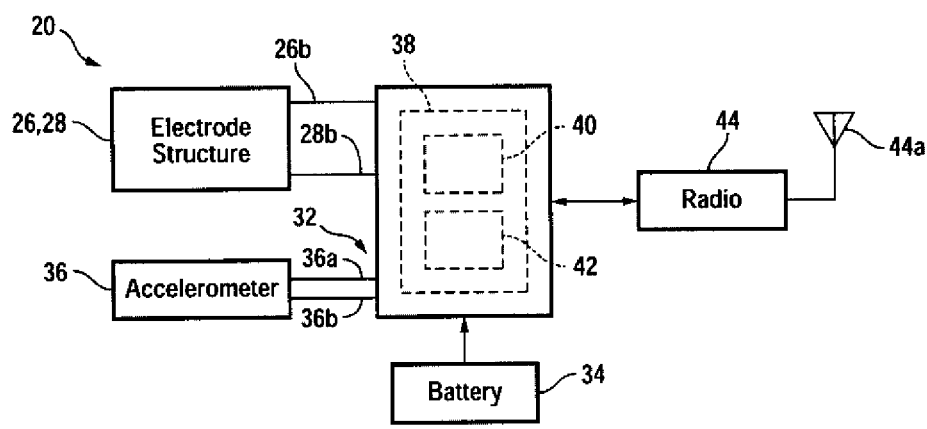
FIG. 5 is a basic block/schematic diagram illustrating electrical and mechanical componentry employed in the system of the invention and incorporated both in the invention embodiment pictured in FIGS. 1-4, inclusive, and in the still-to-be-mentioned, alternative embodiment shown in FIG. 8.

An operative connection between circuit structure 32 and accelerometer 36 is represented in FIG. 5 by conductors 36a, 36b.

Electrodes 26, 28 are operatively connected to circuit structure 32 for bimodal (sensing/stimulating) operation through what may be thought of as bi-directionally employed conductors 26b, 28b, respectively, and these electrodes, circuit structure 32, battery 34, and accelerometer 36 are all appropriately operatively interconnected to function collaboratively in manners shortly to be described.

Appropriate, conventional, analogue-to-digital, and digital-to-analogue converters, not specifically shown in the drawings, are incorporated where needed.

Electrical circuit structure 32, as mentioned generally above, features what is referred to as logic-including, internal-control circuitry, also referred to herein as computer structure, or more simply as a computer, 38, possessing waveform monitoring and recording substructure 40, and optionally (representationally present herein), timing adjustment substructure 42. Preferably, computer 38, which could, if desired, be fully hard-wired to perform its intended functions, is herein incorporated and configured with a microprocessor, or the like, so as to be at least partially, if not fully, algorithmically software-programmable structure-programmable, in the system now being described, not only initially, but, if desired at later times, by close-proximity telemetry communication accommodated through a system-included, conventional, short-range radio 44 having an antenna 44a. Computer 38 also includes a suitable, conventionally designed "state machine" (not specifically, separately illustrated in the drawings) for implementing various important timing controls, as will be explained below herein.

Choices for, and appropriate organizations of, specific electrical circuitry elements, including logic-structure computer-associated elements, and all hard-wired-managed, and/or software-dictated-and-managed, operational "programming" which controls systemic and methodologic functioning of the invention, are designable and includable employing conventional, state-of-the-art devices, algorithms, and other knowledge in the possessions of those persons who are generally skilled in the relevant arts, and for that reason are not specifically detailed herein. The systemic structural descriptions presented herein, as well as the methodological, operational features of the invention discussed, will well arm those generally-skilled persons to practice all aspects of the present invention.

Turning attention now to FIGS. 6A, 6B, 7A, 7B, along with continued references, as appropriate and helpful, to FIGS. 1-5, inclusive, FIG. 6A furnishes, as stated earlier, a frontal view of an internal portion 46 of a subject's anatomy illustrating, generally at 48, preferred, implanted positioning therein proposed for the system 20 pictured in FIGS. 1-4, inclusive. In FIG. 6A, system 20 is simply illustrated by a very evident, generally horizontally disposed, thickened, dark line, and specifically, what is illustrated, is that capsule 24 in this system is placed at a selected surface region 48a on the inferior side of the subject's diaphragm 50. More specifically, capsule 24 is positioned left-laterally in the subject's anatomy, clearly out of contact with the subject's heart 52, and actually in a modest state of compression between the inferior side of diaphragm 50 and the subject's immediately underlying liver, seen generally, and fragmentarily only, at 54. In a very specific sense, capsule 24 is disposed with its electrode face 24b (not specifically seen or marked in FIG. 6A) facing the inferior surface of the diaphragm, with electrodes 26, 28 (also not specifically seen in this figure) directly contacting diaphragmatic surface region 48a.

In relation to what is seen in FIG. 6A, and as was mentioned earlier herein, capsule 24 has been implanted through conventional laparoscopy—a surgical practice which forms no part of the present invention.

Turning attention to FIG. 6B, this figure also shows just-mentioned, internal, anatomical portion 46, and is similar to FIG. 6A, except that it shows an alternative placement in the subject's anatomy for capsule 24 in system 20. In FIG. 6B, capsule 24 has been placed on the superior surface of diaphragm 50 at an implantation position generally shown at 56, and specifically on a selected, diaphragmatic surface region 56a, which has a left-lateral disposition in the subject's anatomy similar to the left-lateral implantation disposition pictured on the underside of diaphragm 50 in FIG. 6A. Here, capsule 24 is disposed with its electrode face 24b (not specifically seen or marked) facing the superior surface of the diaphragm, and with electrodes 26, 28 (also not specifically shown in FIG. 6B) directly in contact with the diaphragm.

In the disposition shown in FIG. 6B for capsule 24, the capsule is slightly compressed between the superior surface of diaphragm 50 and the underside of the subject's left lung 58.

In relation to the positioning shown for capsule 24 in FIG. 6B, and as was mentioned earlier herein, this capsule has been implanted through conventional thoracotomy—another surgical procedure which also forms no part of the present invention.

Turning attention now to FIGS. 8, 9A, 9B, indicated generally at 60 in these three figures, and focusing attention initially here on what is shown in the FIG. 8, is the second, above-mentioned, principal form of the invention, which is a self-powered, implantable, distributed form of the invention—distributed in the sense that it includes a pair of spaced component assemblies 62, 64, operatively interconnected by appropriate, elongate, communication lead structure 66. Except for the fact that this form of the invention has the just-mentioned distributed nature, and the further fact that it's distributed componentry, when implanted in a subject's anatomy as pictured generally in FIGS. 9A, 9B is uniquely associated with this distributed embodiment form, it includes all of the operatively interconnected electrical and mechanico-electrical componentry described above for system form 20—interconnected as illustrated schematically in FIG. 5. Additionally, the performance of system 60 is essentially identical to that of system 20.

Included within component assembly 62 are a cylindrical housing 68, from one side of which projects a spiral-form, diaphragm-attaching electrode 70, and in which is appropriately mounted a three-dimensional accelerometer 72 represented by a small thickened and darkened line in FIG. 8, and next to housing 68, and represented by a small rectangle, another electrode 74 which, together with electrode 70, form the previously mentioned bimodal electrodes. Collectively, electrodes 70, 74 constitute the bimodal electrodes structure discussed above.

Shown immediately to the right of component assembly 62 in FIG. 8, and visually linked to the image of this component assembly by a curved, double-arrow-headed arrow 76, is a symbolic representation 78 of assembly 62, which symbolic representation is employed (as can be seen) in each of FIGS. 9A, 9B to enable a simpler way of picturing there the respective presences of assembly 62 in the anatomical images presented in these two figures.

Electrode 70, the spiral-form electrode, is designed to enable spiral, attachable embedment into the structure of a subject's diaphragm for securing component assembly 62 in place, and in a manner whereby both electrodes 70, 74 will essentially be in contact with a selected surface region in the diaphragm, with accelerometer 72 in an appropriate motion-sensing relationship relative to, and effectively in contact with, the diaphragm.

Lead structure 66 includes conductors (not illustrated in specific detail) which are appropriately connected to electrodes 70, 74, and to accelerometer 72, which conductors extend in the lead structure to component assembly 64.

Component assembly 64 includes all of the system electrical circuitry, the system battery, and the system radio and antenna (not specifically pictured in FIG. 8), such as those, same elements illustrated in FIG. 5. The length of lead structure 66 is a matter of user choice, and will typically be chosen, of course, to accommodate intended implantation disposition of system 60 within a particular subject's anatomy.

Focusing now on FIGS. 9A and 9B, and beginning with what is shown in FIG. 9A, here, one can see that system 60, as was true for the illustration provided in FIG. 6A for system 20, is disposed at previously mentioned implantation position 48 on also previously mentioned inferior diaphragmatic surface region 50a. One will note that only, within system 60, component assembly 62 is shown in FIG. 9A, with lead structure 66 broken away, and component assembly 64 not specifically pictured. A reason for this is that what is important to note with respect to what is seen in FIG. 9A is the diaphragmatic positioning of component assembly 62, with one recognizing that implantation of the other end of system 60, namely, component assembly 64, can be located at the user's choice, and suitably, anywhere in the subject's anatomy below diaphragm 50.

FIG. 9B, which, as has already been mentioned, is very similar to FIG. 6B, shows system 60 disposed at previously mentioned implantation position 56 on also previously mentioned diaphragmatic surface region 50b, located on the superior side of diaphragm 50.

Here, too, lead structure 66 is broken off with component assembly 64 omitted from FIG. 9B, one here recognizing that the installer of system 60 will choose an appropriate, above-the-diaphragm placement site for component assembly 64.

Addressing attention now, briefly, to the implantation dispositions shown in FIGS. 6A, 6B, and 9A, 9B, for systems 20, 60, respectively, which dispositions are left-lateral in the subject's anatomy, and either inferior (preferred) or superior relative to the diaphragm, in each of these dispositions the electrodes and the accelerometers are essentially in direct contact with the described and illustrated surface regions in the diaphragm, out of direct contact with the heart. Additionally, in each of the system dispositions shown in these four figures, the electrodes in the respective systems are well positioned to detect easily heart-associated electrical activity, and the accelerometers are similarly positioned to detect easily heart sounds, and, of course, diaphragmatic movement/motion.

Having now completed descriptions of what is illustrated in FIGS. 6A, 6B, 9A, 9B, I to turn attention to FIGS. 7A and 7B. As a reminder, and as was pointed out in the text above regarding the descriptions of the drawings, in each of FIGS. 7A, 7B, system components of the invention have been omitted so that one can more easily focus on the motion-created nature of, and behaviors associated with, diaphragmatic electrical stimulation produced by operations of the systems of the invention. In each of these two figures, and recognizing that they present enlarged, and very small fragmentary regions drawn from the anatomical presentations seen in FIGS. 6A, 6B and 9A, 9B, the anatomical left side of diaphragm 50 is shown in solid outline in a non-stimulated condition relative to the adjacent anatomical components, and particularly relative to heart 52 and its left ventricle.

As indicated by a downwardly-pointing arrow 80 in FIG. 7A, on the initiation of an electrical stimulating pulse applied to diaphragm 50, the diaphragm moves downwardly rapidly in a caudal direction to a position which is somewhat exaggeratedly illustrated for it in dashed lines at 50A in this figure. This caudal movement of the diaphragm, because of the diaphragm's intimate association with the base of the left ventricle in heart 52, pulls downwardly on this ventricle to produce the position for the lower part of the heart and ventricle shown in dashed lines at 52A in FIG. 7A.

FIG. 7B pictures relevant, moved relationships which exist immediately following the conditions shown in FIG. 7A. More specifically, an upwardly pointing arrow 82 in FIG. 7B shows conditions wherein diaphragm 50 has moved upwardly in a cranial direction to the exaggerated, moved position for it shown in dashed lines at 50B—a diaphragmatic movement which drives upwardly on the underside of the left ventricle in the heart to create a heart and left ventricle moved condition pictured in dashed lines at 52B.

The time-sequential moved conditions pictured in FIGS. 7A, 7B, are, essentially, repeated synchronously in each cardiac cycle of a subject's heart in accordance with what constitutes herein predetermined timing associated with, and triggered by, the sensed occurrence of a valid, electrical or mechanical V-event, sensed either electrically by the bimodal electrode structure functioning in its "one", sensing mode as established for it by operatively connected electrical circuit structure 32, or mechanically by the included system accelerometer. As will be explained shortly, with the system of the invention implanted and operating in a subject's anatomy, and set to "look for", and employ, for example, valid electrical V-events as "triggers" for implementing a cardiac-cycle-synchronized, shortly-to-follow diaphragmatic stimulation, cardiac-cycle-synchronized, stimulation-produced diaphragmatic movements, biphasic in nature as described above, occur in every cardiac cycle, except in what may be referred to as a non-normal cardiac cycle in which there occurs, unexpectedly, an electrical V-event which "looks like", but is not, an appropriate, valid, electrical V-event that presents itself during that cardiac cycle's associated refractory period. More will be said about this special circumstance shortly in relation to what is shown in FIG. 10. The occurrence of such a non-valid electrical V-event within a cardiac cycle's refractory period creates a situation where, in order to protect against lack of efficiency and potential difficulty, no related, next-following electrical stimulation is applied to the diaphragm.

FIGS. 10 and 11, as mentioned earlier, present conventional-style laddergrams which picture, respectively, what are referred to herein as (a) early, or anticipatory, diaphragmatic stimulation (PIDS), and (b) late, or following, diaphragmatic stimulation (PIDS). As just indicated in the preceding sentence, in discussions now following regarding these two drawing figures, as well as in still-to-be-presented discussions respecting FIGS. 12 and 13, the previously identified term PIDS will, at times, be used, in the text (and in the illustrating drawings) to identify diaphragmatic stimulation.

As a preliminary orientation to the manners in which FIGS. 10 and 11 are drawn, each figure includes a pair of vertically spaced, horizontal time lines, labeled "V" and "P", where V stands for a V-event, and P stands, in a shortened manner, for the acronym PIDS (electrical diaphragmatic stimulation). The time lines in these two drawing figures effectively cover four, representative cardiac cycles, and each figure includes, at its lower left side, a self-explanatory, graphical-symbol legend which is associated with the several, and various, graphical indicia that are distributed along the time lines above in the figure.

Except for the specific discussions now to follow which explain certain, important predetermined timing settings pictured in these drawings—settings that relate to notable operations of the system of the invention, I believe that those who are generally skilled in the relevant art will clearly understand the information conveyed by the related sequences of events pictured in these two drawing figures, especially in the context of understanding that operation of the system of the present invention involves cardiac-cycle-synchronized sensing of valid V-events, electrical or mechanical, and the using of such sensed and noted events as triggers for the implementation of a then-following, electrical diaphragmatic stimulation.

Having said this, it should be evident that the upper time line in each of these two drawings pictures, among other things, a sequential series of sensed V-events, and that the lower time line represents respectively associated, thereafter-following PIDS stimulations. Angular, sloping dashed lines which extend in each of FIGS. 10 and 11 downwardly and to the right between the upper and lower time lines relate to what are referred to herein as V-PIDS timing periods or delays, and also as predetermined timed relationships—parameters that are functional in the operation of the system of the invention in accordance either with (a) user-selected presetting of these delays, (b) used re-setting of these delays after a period of system operation, and/or (c) on-the-fly, system-internal, systemically self-effected adjustments of such delays, where such system-internal adjustments are permitted (i.e., user-selectively accommodated by appropriately system-included, conventional logic programming). In all embodiments of the system of the invention that are currently contemplated, adjustments in the V-PIDS delay parameter, both in a necessary pre-setting manner with the system in an implanted (or not) condition, and later, if desired, in a system-implanted re-setting situation, are permitted via remote telemetry, or otherwise. The graphically illustrated V-PIDS delays "represented" by the sloping, dashed lines in FIGS. 10 and 11, are actually measureable, i.e. visualizable, graphically in these figures in a manner and direction which is horizontally parallel to the time lines, and not angularly.

Saying a little bit more in an orientation sense regarding FIGS. 10 and 11, the relational, sensed V-events and associated stimulation occurrences pictured may now be thought of as being presented, for further and discussion illustration purposes herein, in the context of an implementation of the invention wherein it is valid, electrical V-events have been selected to be the markers, i.e., the triggers, for PIDS stimulation.

Continuing with description relating to matters shown graphically in FIGS. 10 and 11, there are two, important, and importantly related, timing periods that are taken into account in the practice of the present invention, one of which, the V-PIDS delay period, has just been discussed, and the other of which is the length of the so-called refractory period that exists in each of a subject's cardiac cycles, immediately following a sensed, valid V-event in that cycle. In these two figures, the relevant refractory periods are represented graphically by elongate, vertically-thin, horizontal rectangles distributed along the time lines. The graphical legends presented in FIGS. 10 and 11 make clear which illustrated "rectangles" these are.

Timing operations, with respect to these two time periods are under the control of two, logic-based timers that are realized/implemented, and "operated", so-to-speak, in appropriate timing-tracking manners by the previously-mentioned, included-logic state machine in its association with the electrical-circuitry-included logic, or computer, structure.

The time-period associated with the timer which deals with tracking a cardiac-cycle refractory period, a period which, as was just mentioned, begins immediately following the sensing of a chosen, valid V-event, involves subject-specific data that is pre-known, for example, to a medical practitioner using the system of the invention, and who is familiar with the particular subject to be equipped with the system. For a given subject, and as a precursor typically to implantation, and certainly to activation, of the system of the present invention with respect to that subject, two pieces of subject-specific information are relevant to establishing what will be, at least initially, a preset duration for a timed refractory period. Required for this determination are (1) knowledge of the expected likely heart-rate range of the subject, and (2) knowledge regarding the specifically chosen event (electrical in the situation now being discussed) in each of the subject's cardiac cycles which will be treated as the valid V-event from which a measured time will be observed to determine the application of a following, diaphragmatic stimulation. In the description now underway with respect to FIGS. 10 and 11, and, in fact, in the operational description of the system and methodology of the invention still to come, all operational behavior will be described, for illustration purposes, in the setting of a pre-selection having been made for the detected onset of the electrical R wave in each cardiac cycle being the valid, triggering V-event. A conventional, appropriately programmed, EGC-watching approach is used herein to detect this onset in relation to ECG electrical information regularly sensed by the system bimodal electrode structure functioning in its "one", sensing mode under the control of the system electrical circuit structure.

Of the two, alternative V-PIDS delay-time possibilities contemplated for practice of the present invention, I have found that, in most applications, so-called early PIDS stimulation is preferable, and it is for this reason that FIG. 10, in the two-drawing-figure, pictorial-numeric sequence which has been selected for the presentations in the drawings of FIGS. 10 and 11, has been chosen to illustrate such stimulation. Early PIDS stimulation, and the relevant V-PIDS time delay associated with it, lead effectively to a condition for the application of diaphragmatic stimulation at the beginning of a short time interval which lies, in time, as a precursor to the onset of an anticipated V-event in a particular cardiac cycle (to be explained). In a manner of thinking, therefore, one can imagine that the actual (precursor) time gap existing between such early PIDS stimulation and the shortly following onset of a valid, "anticipated", and soon to be next-sensed, valid V-event constitutes a negative time interval in the cardiac cycle where stimulation is to take place. Because of this, and because such stimulation must be measured from an already-having-occurred, sensed valid V-event, the system and methodology of the present invention perform this measurement beginning from the just previously sensed, valid V-event in the immediately prior cardiac cycle.

Continuing with this thought, and recognizing that proper establishment, for successful systemic operation, in an early-PIDS manner of functioning, of an appropriate a V-PIDS delay interval following the occurrence of the sensed V-event which is employed to trigger stimulation action, it is important to know, and this is done by an averaging technique, just how to anticipate a next-expected valid V-event. To this end, and employing conventional algorithmic programming well-known to those generally skilled in the relevant art, once the system of the invention has begun its operation, and after the first few cardiac cycles associated with that operation, a running average is performed based (in the present system implementation) upon the four, prior cardiac cycles to assess an average timing expected between successive, valid V-events. This average is "made known" within the logic componentry in the system for every successive cardiac cycle after the first four cycles which mark the beginning of system operation, and accordingly, on-the-fly, so-to-speak, a V-PIDS timing delay, "represented" in FIG. 10 by the previously-mentioned, sloping dashed lines, is calculated by performing, effectively, a subtraction, from the then-available averaged timing determined between successive, valid V-events, of the brief, precursor interval (just mentioned above) the beginning of which is intended to define the moment of triggering of a PIDS stimulation in anticipation of the expected, very shortly following, next-valid, and sensed, V-event.

If desired, the system of the present invention may be structured in a conventional manner to allow the making of a change associated with early PIDS stimulation through the making of a change in settings available to the system describing, differently, the short precursor (subtraction anticipatory) interval just discussed.

Continuing with the discussion regarding what is shown in FIG. 10, this figure illustrates the potential problem-creating possibility (mentioned earlier) of an errant V-event which occurs, outside of normal cardiac behavior, within a particular cardiac cycle's refractory period. Looking specifically toward the right side of what is shown in FIG. 10, seen along the upper time line is a presentation of the occurrence of such an errant V-event which has taken place during the illustrated cycle's refractory period. To the right of this indication in the upper time line, and specifically below the associated, lower time line, text is presented indicating that there is not to be an immediately-next-following PIDS stimulation—a protective measure, as noted earlier.

Directing attention now to FIG. 11, and as a reminder about the nature of the teaching which is evident in this figure, FIG. 11 describes what has been referred to as a late PIDS stimulation situation. This situation is very easy to understand, in the sense that to implement it, all that is required is a system setting for a predetermined V-PIDS delay time which is very short, typically, and which, within a common cardiac cycle, shortly follows a sensed, valid V-event.

In relation to a final point to mention regarding FIGS. 10 and 11, small blackened rectangles distributed, as shown, along the V time lines in these figures mark short, conventionally-system-implemented blanking periods that are created and exist to prevent a stimulation pulse from producing unintended cardiac electrical activity. In the early PIDS situation, these blanking periods fall outside of the cardiac-cycle refractory periods. In the late PISD situation, they occur during refractory periods.

Turning attention now to FIGS. 12 and 13, FIG. 12 illustrates, along two, vertically spaced, time-related time lines, (1) an upper graphical trace of an ECG waveform received from subject-implanted system electrodes, picturing a large plurality of successive subject cardiac cycles, including the evident presences of cycle-synchronized PIDS stimulations, and (2) a lower graphical trace of related output information received from the implanted-system-included accelerometer showing both the lower-frequency characteristic of normal respiration, and the superimposed, higher-frequency, cardiac-cycle-synchronized, biphasic diaphragmatic motions that have resulted from the PIDS stimulations shown above in the electrically illustrated cardiac cycles. The waveforms of these biphasic diaphragmatic motions, captured and recorded, as they are, for later reporting by the system of the present invention, are importantly useful for helping a medical professional, in the setting of actually seeing the waveform of what biphasic, diaphragmatic, stimulation-produced motion looks like, to assess both, ultimately, the quality of a subject's hemodynamic performance, and also the quality of enhancement-assistance thereof furnished by the invention.

FIG. 13 furnishes an enlarged, and time-stretched, view of fragments of the two traces presented in FIG. 12, selected from the region in FIG. 12 marked by the two, vertical, laterally-spaced dashed lines that mark a display region for FIG. 13 designated 84 in FIG. 12.

What can be seen by looking at these two drawing figures, very clearly, is that each illustrated PIDS stimulation, which is short-term and pulse-like in nature, produces, in the represented subject's diaphragm's movement, a related, cardiac-cycle-synchronized, relatively high frequency, biphasic, caudal-followed-by-cranial movement of the diaphragm. It is this relatively high-frequency, biphasic, diaphragmatic motion, caudal-followed-by-cranial in nature, which, in the context of there being a properly waveform-shaped motion of the diaphragm, enhances a subject's hemodynamic performance through the effective delivery of that diaphragmatic motion to the underside of the heart's left ventricle, as explained earlier.

As was mentioned earlier herein, internal programming, hard-wired and/or algorithmically programmed/programmable, is in many ways completely conventional in nature in terms of specific tasks that are performable during operation of the system of the present invention. While, as has already been mentioned above, there are certain settings that, preferably, are introduced as initial settings introduced to the circuitry logic structure provided in the system of the invention—put there into place by the system user/installer/implanter—there are certain operational features and re-settings which may, over time, be adjusted and/or introduced, either remotely through short-range telemetry accommodated by radio 44, or automatically internally in association with a systemic capability, if such a capability is selectively provided, for the system to self-monitor and self-adjust various aspects of its own activities. With regard to telemetry-implemented operational modifications, as well as potentially internally self-implemented operational modifications, again, those generally skilled in the relevant arts will know how to do this based upon the systemic and methodologic descriptions of the invention presented in this text and pictured in the associated drawing figures.

Regarding such potential modifications, and various associated activities, I recognize to be a very interesting category of easily-accomplishable self-modification, the making of changes in the above-identified and discussed V-PIDS time-delay settings. As was also pointed out earlier herein, importantly, with respect to self-implemented operational modifications, the system and methodology of the present invention do not allow for the self-implemented making of any changes in the character of electrical diaphragmatic stimulation. It is, of course, entirely possible for a system user who is monitoring a subject's hemodynamic performance condition, to make such modifications remotely by telemetry.

An important and special feature of the present invention involves the capturing and recording of accelerometer data associated with the nature of actual, stimulation-produced diaphragmatic biphasic movement. This capture and recording, in association with an importantly implemented, and uniquely contemplated, comparison of captured, actual diaphragmatic motion waveforms with a system-stored, carefully chosen, reference waveform, yields reportable information that allows a system user to initiate stimulation adjustments to improve matters. This comparison activity produces system-stored comparison data which is retrievable by telemetry to furnish valuable confirmatory evidence of the viability of the implemented diaphragmatic stimulation respecting the maximizing and achieving of hemodynamic performance.

Before describing a typical operation of the system with respect to a particular subject, let us turn attention to FIG. 14 in the drawings which illustrates, in block/schematic form, both the basic, and a modified, form of the architecture of the methodology of the present invention. The "overall" archaeology, as shown in FIG. 14, is illustrated generally at 86. It includes, as steps represented in block form, six different blocks, including block 88 (Sensing), block 90 (Applying), block 92 (Monitoring), block 94 (Comparing), block 96 (Recording), and block 98 (Choosing). Blocks 88-96, inclusive, are drawn each with a solid-line outline to signify that they describe, effectively, the basic, or core, methodology of the invention. Block 98, which is outlined with a dashed line, represents one modified form of the invented methodology. Reading from left to right in FIG. 14, the several blocks there pictured are connected in the order of associated behaviors, with arrow-headed, right-pointing lines connecting these blocks, as shown, to symbolize the flow of methodologic activity.

The present invention thus offers a method for improving the hemodynamic performance of a subject's heart including, from adjacent a selected surface region in the subject's diaphragm which is out of contact with the heart, (1) Sensing and noting (Block 88) the presences in the subject's cardiac cycles of a selected one of (a) per-cycle valid electrical, and (b) per-cycle valid mechanical, V-events, (2) based upon such sensing, and upon noting each of such selected, V-event presences, Applying (Block 90), in a predetermined timed relationship to such a noting, associated, asymptomatic electrical stimulation directly to the diaphragm, preferably at the selected diaphragmatic surface region, for the purpose of triggering biphasic, caudal-followed-by-cranial motion of the diaphragm, (3) following the applying step, Monitoring (Block 92) the waveform of resulting diaphragmatic motion, (4) after performing the monitoring step, Comparing (Block 94) the monitored diaphragmatic-motion waveform with a reference, diaphragmatic-motion waveform, and (5) on completion of the comparing step, Recording (Block 96) the monitored, diaphragmatic-motion waveform for later review.

The invention methodology, in a modified form, further includes (1) Choosing (Block 98) the selected diaphragmatic surface region to be on one of (a) the inferior, and (b) the superior, side of the diaphragm, and (2) choosing the selected, per-cycle valid V-event whereby, if it is to be electrical, it is one of (a) the R wave, and (b) the Q wave, and if mechanical, it is the S1 heart sound.

Presenting now a description of typical system preparation, implantation, and operation with respect to a particular, selected subject, this description will be based upon the implantation in a subject of that form of the system of the invention which is pictured in FIGS. 1-5, inclusive, and installed as illustrated in FIG. 6A. Further, this description will be based upon a predetermination that the triggering of diaphragmatic stimulation will be based upon the sensing, in the subject's cardiac cycles, of valid electrical V-events, with the chosen, valid electrical V-event being the onset of the R wave. The operational description which now follows will also rest upon a pre-decision that early PIDS stimulation is what is to take place, and that until, as will shortly be described, a more concrete idea is reached for defining an exact V-PIDS delay interval, the system logic structure-effectively, the state machine portion of this structure—will be "told" to begin with a V-PIDS delay time of zero.

Also initially determined, and this, before system implantation, is what kind of a timing interval to pre-assign to the refractory period timer operated by the state machine, and this timing interval will be based upon subject-specific information drawn from pre-knowledge about the subject's expected likely heart-rate range, and typical refractory period time length beginning with the onset of the R wave, and ending with the end of that refractory period.

Also completely predetermined will be system settings that establish, essentially fixedly, the character of electrical PIDS stimulation designed to be clearly asymptomatic in nature.

Much of this pre-implantation information, relevant to preparing the system of the invention for best-possible work with the selected subject, will involve a further category of information, known to the appropriate medical personnel, regarding how to assess, with the system operating, maximally-achievable, enhanced hemodynamic performance.

With system pre-settings based upon the just-described preliminary choices made, the system is implanted appropriately, as illustrated in FIG. 6A, and is switched into operation, with the system user immediately collecting appropriate data to assess needed adjustment, from zero, to establish in the state machine the most appropriate early-PIDS time interval now to be "reset" for per-cycle calculation of the important V-PIDS delay period. Those persons skilled in the medical arts will know well how to make this assessment, and with this knowledge in hand, will, through short-range telemetry, introduce into the logical structure of the state machine, as just mentioned, the appropriate V-PIDS delay information.

With the early PIDS, V-PIDS delay period thus set, the system of the invention now simply regularly estimates, through the on-the-fly averaging technique described above, a proper point in time, following the sensing in one cardiac cycle of a valid electrical V-event, to apply diaphragmatic stimulation in the following cardiac cycle appropriately, and shortly, before the next-sensed, valid electrical V-event. Errant electrical V-events sensed during a cardiac cycle's refractory period will not be used to trigger stimulation. Valid electrical V-event sensing will take place through the system-included, bimodal electrode structure placed by the system electrical circuit structure in its "one", sensing mode, and electrical stimulation delivered to the diaphragm, under the controlling influence of the system electrical circuit structure, will be delivered by the same, efficiently employed, bimodal electrode operating in its "other", stimulating mode. Interesting to note here, specifically, is that the incorporation in the system of the present invention of the described, bimodal electrode structure offers the simplicity of utilizing simply one pair of electrodes to perform, seriatim, electrical-activity sensing, and electrical diaphragmatic stimulation.

Each sensed, valid electrical V-event will result in asymptomatic electrical stimulation of the subject's diaphragm to produce high-frequency, biphasic, caudal-followed-by-cranial diaphragmatic movement, and this cycle-by-cycle activity will synchronously drive the left ventricle of the subject's heart in a biphasic, pumping-assist manner which will enhance hemodynamic performance as described above.

The system accelerometer will accurately follow the stimulation-induced biphasic diaphragmatic movement which is associated with each diaphragmatic stimulation, and will, cycle-by-cycle, communicate to the electrical circuit structure the mentioned, related, diaphragmatic-motion confirmation signal whose associated waveform will be compared with that of the mentioned, carefully-chosen reference waveform to generate, for storage and later retrieval, cardiac-cycle-by-cardiac-cycle waveform comparison data.

All of this activity will be occurring, as mentioned, entirely synchronously with the subject's cardiac-cycle-by-cardiac-cycle heart rate.

The operational description just presented, wherein the preselected, valid V-event has been chosen to be electrical and to be associated specifically with the detected onset of a cardiac cycle R wave, closely also describes both (a) an alternative system operation based upon selection of the Q wave as being the valid electrical V-event, and (b) another, alternative system operation based, instead, on mechanical V-event sensing, wherein a selected, valid mechanical V-event is chosen to be the S1 heart sound—an event which will be sensed by the system-included accelerometer. In this latter, alternative operational setting, the accelerometer plays the dual roles of sensing valid V-events, and tracking and reporting on stimulation-produced diaphragmatic movements.

Accordingly, while two, important, principal, systemic embodiments of the invention have been illustrated and described herein in detail, and certain modifications suggested, and while, also, preferred and modified forms of system-implemented methodology and system operation have been discussed and illustrated, I recognize that other variations and modifications may come to the minds of those generally skilled in the relevant arts, are possible, and may be made without departing from the spirit of the invention, and it is my intention that the following claims to invention will all be interpreted to have scopes which will embrace such other variations and modifications.

What is claimed is:

1. A method for improving hemodynamic performance of a heart through electrical stimulation of a diaphragm, the method comprising:
   detecting a cardiac event in a cardiac cycle of a patient;
   delivering an electrical stimulation therapy to a diaphragm of the patient timed to the detection of the cardiac event in the cardiac cycle of the patient, wherein the electrical stimulation therapy is defined by a plurality of stimulation parameters;
   monitoring an intrathoracic pressure associated with an intrathoracic cavity of the patient to determine whether an adjustment of one or more of the plurality of stimulation parameters is warranted; and
   adjusting one or more of the stimulation parameters based on the monitoring.

2. The method of claim 1, wherein detecting a cyclic cardiac event comprises sensing electrical cardiac activity through one or more of a plurality of electrodes placed adjacent to the diaphragm or in direct contact with the diaphragm.

3. The method of claim 1, wherein electrical stimulation is applied to the diaphragm through at least one of a plurality of electrodes placed adjacent to the diaphragm or in direct contact with the diaphragm.

4. The method of claim 1, wherein monitoring a pressure associated with the intrathoracic cavity comprises:
   obtaining a signal indicative of the intrathoracic pressure;
   deriving a measure of intrathoracic pressure from the obtained signal;
   evaluating the measure of intrathoracic pressure against a baseline measure of intrathoracic pressure; and
   determining to adjust one or more of the stimulation parameters based on the evaluation.

5. The method of claim 4, wherein the signal indicative of the intrathoracic pressure is obtained from a pressure sensor implanted within the intrathoracic cavity of the patient.

6. The method of claim 5, wherein the pressure sensor comprises one of an accelerometer, a motion sensor, and a heart sound sensor.

7. An apparatus for affecting a pressure within an intrathoracic cavity of a patient, the apparatus comprising:
   one or more electrodes configured for placement on or near a diaphragm of the patient;
   a pressure measurement source configured to provide a signal indicative of a pressure within an intrathoracic cavity of the patient; and
   a controller configured to:
      detect a cardiac event in a cardiac cycle of the patient based on a signal obtained from the one or more electrodes;
      deliver an electrical stimulation therapy to a diaphragm of the patient through the one or more electrodes, wherein delivery of the electrical stimulation therapy is timed to the detection of the cardiac event in the cardiac cycle, and the electrical stimulation therapy is defined by a plurality of stimulation parameters;

monitor a pressure associated with the intrathoracic cavity based on the signal provided by the pressure measurement source, to determine whether an adjustment of one or more of the plurality of stimulation parameters is warranted; and adjust one or more of the stimulation parameters based on the monitoring.

8. The apparatus of claim 7, wherein:

the pressure measurement source is a pressure sensor and the signal indicative of the pressure corresponds to a signal representing one of intrathoracic pressure, right atrial pressure, right ventricular pressure, left ventricular pressure, aortic pressure, and pulmonary artery pressure, and the controller monitors a pressure associated with the intrathoracic cavity by being further configured to:

derive a measure of interest from the signal indicative of a pressure within an intrathoracic cavity of the patient;

evaluate the measure of interest against a baseline measure of interest; and determine to adjust one or more of the stimulation parameters based on the evaluation.

9. The apparatus of claim 8, wherein the measure of interest is a pressure measurement at or near a fiducial point within a cardiac cycle, and the baseline measure of interest is one of: a) a pressure measurement at or near the fiducial point within a cardiac cycle, derived from a previously obtained signal indicative of the pressure, or b) a nominal value of the measure of interest.

10. The apparatus of claim 9, wherein the fiducial point is located at or near a cardiac event, or a period after a cardiac event.

11. The apparatus of claim 8, wherein:

the controller evaluates the measure of interest against a baseline measure of interest by being further configured to determine if the measure of interest represents an increase in negative pressure relative to the baseline measure of interest or a decrease in negative pressure relative to the baseline measure of interest, and the controller determines to adjust one or more of the stimulation parameters based on the evaluation, by being further configured to:

adjust one or more of the stimulation parameters when the measure of interest represents a decrease in negative pressure, and maintain the stimulation parameters when the measure of interest represents an increase in negative pressure or a steady state negative pressure.

12. The apparatus of claim 7, wherein:

the pressure measurement source is a motion sensor and the signal indicative of the pressure corresponds to a signal representing one of movement of the diaphragm or heart sounds, the controller monitors a pressure associated with the intrathoracic cavity by being further configured to detect an event of interest from the signal indicative of the pressure, the event of interest corresponding to a respiration cycle event, and the controller adjusts at least one of the stimulation parameters by being configured to:

withhold delivering a stimulation pulse timed to be delivered at or near a time of the respiration cycle event; and change one or more parameters of a stimulation pulse timed to be delivered at or near a time of the respiration cycle event.

13. The apparatus of claim 12, wherein the respiration cycle event is an end of an inspiration stage of a respiration cycle.

14. A method for improving hemodynamic performance of a heart through electrical stimulation of a diaphragm, the method comprising:

detecting a cardiac event in a cardiac cycle of a patient;

delivering an electrical stimulation therapy to a diaphragm of the patient timed to the detection of the cardiac event in the cardiac cycle of the patient, wherein the electrical stimulation therapy is defined by a plurality of stimulation parameters;

obtaining an intrathoracic pressure measurement at or near a fiducial point within the cardiac cycle;

evaluating the intrathoracic pressure measurement against a baseline; and adjusting one or more of the stimulation parameters based on the evaluation.

15. The method of claim 14, wherein the baseline is one of: a) a pressure measurement at or near the fiducial point within a cardiac cycle, derived from a previously obtained signal indicative of a pressure measurement at or near the fiducial point within a prior cardiac cycle, or b) a nominal value.

16. The method of claim 14, wherein obtaining an intrathoracic pressure measurement at or near a fiducial point within the cardiac cycle comprises:

obtaining a signal indicative of the intrathoracic pressure; and deriving the intrathoracic pressure measurement from the obtained signal.

* * * * *